(12) United States Patent
Kunnari et al.

(10) Patent No.: US 8,686,164 B2
(45) Date of Patent: Apr. 1, 2014

(54) CRYSTALLIZATION OF 4'-EPIDAUNORUBICIN HYDROCHLORIDE

(75) Inventors: Tero Kunnari, Aschaffenburg (DE); Holger Bindernagel, Gelnhausen (DE); Sascha Weiser, Maintal (DE); Andrew Lupton, Gelnhausen (DE); Stefan Wallert, Seligenstadt (DE)

(73) Assignee: Heraeus Precious Metals GmbH & Co. KG, Hanau (DE)

( * ) Notice: Subject to any disclaimer, the term of this patent is extended or adjusted under 35 U.S.C. 154(b) by 0 days.

(21) Appl. No.: 13/394,738

(22) PCT Filed: Sep. 8, 2010

(86) PCT No.: PCT/EP2010/005498
§ 371 (c)(1),
(2), (4) Date: May 14, 2012

(87) PCT Pub. No.: WO2011/029576
PCT Pub. Date: Mar. 17, 2011

(65) Prior Publication Data
US 2012/0232291 A1 Sep. 13, 2012

(30) Foreign Application Priority Data
Sep. 8, 2009 (EP) .................................... 09011459

(51) Int. Cl.
*C07D 315/00* (2006.01)
(52) U.S. Cl.
USPC ........................................................ 549/419
(58) Field of Classification Search
USPC ........................................................ 549/419
See application file for complete search history.

(56) References Cited

U.S. PATENT DOCUMENTS

| 4,112,076 A | * | 9/1978 | Arcamone et al. ............... 514/34 |
| 4,345,068 A | * | 8/1982 | Suarato et al. .................. 536/6.4 |
| 4,861,870 A | | 8/1989 | Oppico et al. |
| 5,874,550 A | | 2/1999 | van der Rijst et al. |
| 5,945,518 A | | 8/1999 | Bigatti et al. |

OTHER PUBLICATIONS

Zubric, The Organic Chem Lab Survival Manual, John Wiley & Sons, 1984.*
Written Opinion issued Jul. 31, 2012 in SG Application No. 201201094-8.
Int'l Search Report issued on Jan. 14, 2011 in Int'l Application No. PCT/EP2010/005498.
Extended EP Search Report issued on Mar. 3, 2010 in EP Application No. 09011459.6.
Arcamone, Federico et al, "Synthesis and antitumor properties of new glycosides of daunomycinone and adriamycinone", Journal of Medicinal Chemistry, vol. 18, No. 7, pp. 703-707, (1975).
Boivin, J. et al, "Substitutions of allylic esters: preparation of 3-aminoglycals and their acid-catalyzed glycosidation . . . ", Carbohydrate Research, vol. 79, No. 2, pp. 193-204, (1980).
Partial European Search Report issued Aug. 6, 2013 in EP Application No. 13002444.1.

* cited by examiner

*Primary Examiner* — Nizal Chandrakumar
(74) *Attorney, Agent, or Firm* — Panitch Schwarze Belisario & Nadel LLP

(57) ABSTRACT

4'-epidaunorubicin hydrochloride is provided in a crystalline form which is stable and readily soluble. A process of producing the crystalline form includes crystallizing 4'-epidaunorubicin hydrochloride in a solvent system including (a) solvent A selected from $C_1$ and $C_2$ halogenated solvents and mixtures thereof, (b) solvent B selected from $C_1$-$C_5$ straight and branched alcohols and mixtures thereof, and (c) solvent C selected from $C_1$-$C_5$ straight and branched alcohols and mixtures thereof, wherein solvent C is selected to provide lower solubility to 4'-epidaunorubicin hydrochloride than solvent B.

12 Claims, 2 Drawing Sheets

CRYSTALLIZATION OF 4'-EPIDAUNORUBICIN HYDROCHLORIDE

CROSS-REFERENCE TO RELATED APPLICATIONS

This application is a Section 371 of International Application No. PCT/EP2010/005498, filed Sep. 8, 2010, which was published in the English language on Mar. 17, 2011, under International Publication No. WO 2011/029576 A1 and the disclosure of which is incorporated herein by reference.

BACKGROUND OF THE INVENTION

The present invention relates to crystalline 4'-epidaunorubicin hydrochloride and a process for the production thereof.

Anthracyclines comprise a large group of naturally occurring bioactive compounds. Several anthracyclines are used in clinics as anticancer chemotherapeutic drugs. Examples of clinically important substances are daunorubicin, doxorubicin, idarubicin, epirubicin, pirarubicin, aclarubicin, caminomycin, and zorubicin. Anthracyclines can be produced either by chemical synthesis or by fermenting microorganisms. They are used as such (for example, aclarubicin, daunorubicin and caminomycin) or are semi-synthetic derivatives of other anthracyclines (such as epirubicin, idarubicin, doxorubicin, pirarubicin, and zorubicin). Anthracyclines are effective against leukemia and various solid cancerous tumors. Worldwide, the most used anthracyclines are doxorubicin and epirubicin. Epidaurorubicin is the key-intermediate in the synthesis of epirubicin.

U.S. Pat. Nos. 4,112,076; 4,345,068; 4,861,870; 5,945,518; and 5,874,550 disclose the preparation of epirubicin hydrochloride and its use as an anticancer agent.

Currently, the major method for purifying 4'-epidaunorubicin hydrochloride is amorphous precipitation thereof from a solution by addition of an antisolvent. Usually, in this method, a basic solution of epidaunorubicin is treated with methanolic hydrochloric acid to adjust the pH value in a range between 2 and 5, and subsequently 4'-epidaunorubicin hydrochloride is precipitated by addition of an ether.

U.S. Pat. No. 4,345,068 discloses precipitation of 4'-epidaunorubicin hydrochloride from a chloroform extract using methanolic hydrochloric acid. Although referred to as "crystallization," this process does not produce crystalline, but amorphous 4'-epidaunorubicin hydrochloride.

Boivin et al., "Substitutions of allylic esters: preparation of 3-aminoglycals and their acid-catalyzed glycosidation. Use in the partial synthesis of glycosides of the anthracycline group," *Carbohydrate Research*, 79 (2):193-204 (1980) disclose precipitation of 4'-epidaunorubicin hydrochloride from ethanol/ether. This process has also been found to produce amorphous, not crystalline 4'-epidaunorubicin hydrochloride.

Amorphous precipitation of 4'-epidaunorubicin hydrochloride, however, has the drawback that the precipitated 4'-epidaunorubicin hydrochloride is only purely soluble and often purified unsatisfactorily.

BRIEF SUMMARY OF THE INVENTION

Therefore, the problem to be solved by the present invention is the provision of a simple process for the purification and crystallization of 4'-epidaunorubicin hydrochloride, which allows for 4'-epidaunorubicin hydrochloride to be crystallized in a form in which it is stable and readily soluble.

This problem is solved by a process for crystallizing 4'-epidaunorubicin hydrochloride which process comprises crystallizing 4'-epidaunorubicin hydrochloride in a solvent system including:
a) solvent A which is selected from the group consisting of $C_1$ and $C_2$ halogenated solvents and mixtures thereof;
b) solvent B which is selected from the group consisting of $C_1$-$C_5$ straight and branched alcohols and mixtures thereof; and
c) solvent C which is selected from the group consisting of $C_1$-$C_5$ straight and branched alcohols and mixtures thereof, wherein solvent C is selected to provide lower solubility to 4'-epidaunorubicin hydrochloride than solvent B.

By this process, crystalline 4'-epidaunorubicin hydrochloride is produced.

The method of the present invention makes use of 4'-epidaunorubicin hydrochloride as a starting material. The origin and the form of 4'-epidaunorubicin hydrochloride are not further restricted. For example, 4'-epidaunorubicin hydrochloride can be used which is produced from precursors in a preceding chemical synthesis. Also, commercially available 4'-epidaunorubicin hydrochloride can be used which is to be further purified. It is also possible to use 4'-epidaunorubicin hydrochloride which is produced by use of suitable microorganisms and converted into the corresponding hydrochloride in a subsequent step. In particular, it is possible to use as a starting material 4'-epidaunorubicin hydrochloride which contains impurities, for example, impurities which are the result of preceding synthesis steps.

4'-epidaunorubicin hydrochloride is crystallized in a solvent system comprising solvents A, B and C which differ from each other. Therefore, the solvent system referred to herein comprises at least three different kinds of solvents.

Solvent A is selected to have the capability to dissolve 4'-epidaunorubicin hydrochloride. As for its structure, solvent A is selected from the group consisting of $C_1$ and $C_2$ halogenated solvents and mixtures thereof. Solvent A can be a single solvent or a mixture of solvents, but is preferably a single solvent. Generally, as solvent A every kind of solvent can be used as long as it has one or two carbon atoms, comprises at least one halogen atom and is suitable to dissolve 4'-epidaunorubicin hydrochloride. Preferably, solvent A contains 1-3 and more preferably 2 or 3 halogen atoms. As halogens, chlorine and bromine are preferred. The halogen atoms can be the same or different. For example, solvent A can be a compound which has at least one chlorine atom and/or at least one bromine atom. It is preferred that the halogen atom(s) present in solvent A is a (are) chlorine atom(s). The compound or compounds used as solvent A can contain further functional groups in addition to the halogen atom(s). On the other hand, it may be preferred that solvent A does not contain such further functional group(s). According to a preferred embodiment, solvent A is a saturated compound and thus does not contain a double bond. It can furthermore be preferred that solvent A has only one carbon atom. Preferably, solvent A is selected from the group consisting of, dichloromethane, dibromomethane, chloroform, bromoform, dichloroethanes (such as 1,1-dichloroethane or 1,2-dichloroethane), dibromoethanes (such as 1,2-dibromoethane), trichloroethanes (such as 1,1,1-trichloroethane or 1,1,2-trichloroethane), tetrachloroethanes (such as 1,1,2,2-tetrachloroethane), and mixtures thereof. More preferably, solvent A is selected from chloroform, dichloromethane and mixtures thereof.

Solvent B is selected on its ability to purify 4'-epidaunorubicin hydrochloride from common impurities. It is selected from the group consisting of $C_1$-$C_5$ straight and branched alcohols and mixtures thereof. Solvent B can be a single solvent or a mixture of solvents, but is preferably a single solvent. Every alcohol having a $C_1$-$C_5$ carbon skeleton can be used as solvent B, as long as it is able to allow for purification of 4'-epidaunorubicin hydrochloride. In particular, solvent B can be a monoalcohol or a polyalcohol. Furthermore, solvent B includes alcohols having further functional groups in addition to the hydroxyl group(s). It may be preferred, however, that solvent B have no further functional groups. Furthermore, it may be preferred that solvent B is a saturated compound and therefore does not contain double or triple bonds. According to a preferred embodiment, solvent B is selected from the group consisting of $C_1$-$C_3$ straight and branched alcohols and mixtures thereof. According to a further preferred embodiment, solvent B is selected from the group consisting of $C_1$ straight and branched alcohols, $C_2$ straight and branched alcohols, $C_3$ straight alcohols and mixtures thereof. Most preferably, solvent B is selected from the group consisting of methanol, ethanol, 1-propanol and mixtures thereof.

Solvent C is selected to be an antisolvent to 4'-epidaunorubicin hydrochloride. It is selected from the group consisting of $C_1$-$C_5$ straight and branched alcohols and mixtures thereof. Solvent C can be a single solvent or a mixture of solvents, but is preferably a single solvent. Solvent C is also selected to provide lower solubility to 4'-epidaunorubicin hydrochloride than solvent B. In this context, it is submitted that it is within the expert knowledge of a person skilled in the art, to identify from the alcohols described herein as solvent C those alcohols which provide lower solubility to 4'-epidaunorubin hydrochloride than solvent B. For example, the skilled person may dissolve 4'-epidaunorubin hydrochloride in a solvent selected from the group consisting of $C_1$-$C_5$ straight and branched alcohols and mixtures thereof, and determine the dissolution capacity of this solvent for 4'-epidaunorubin hydrochloride. In a next step, the skilled person may dissolve 4'-epidaunorubin hydrochloride in a different solvent selected from the group consisting of $C_1$-$C_5$ straight and branched alcohols and mixtures thereof, and determine the dissolution capacity of this solvent for 4'-epidaunorubin hydrochloride. From the two kinds of solvents examined, the skilled person designates as solvent B the alcohol(s) in which the solubility of 4'-epidaunorubin hydrochloride is higher. Accordingly, he designates as solvent C the alcohol(s) in which the solubility of 4'-epidaunorubin hydrochloride is lower. Every alcohol having a $C_1$-$C_5$ carbon skeleton can be used as solvent C as long as it is able to act as an antisolvent to 4'-epidaunorubicin hydrochloride. For example, solvent C can be a monoalcohol or a polyalcohol. Furthermore, solvent C includes alcohols having further functional groups in addition to the hydroxyl group(s). It may be preferred, however, that solvent B have no further functional groups. Furthermore, it may be preferred that solvent C is a saturated compound and therefore does not contain double or triple bonds. According to a preferred embodiment, solvent C is selected from the group consisting of $C_3$-$C_5$ straight and branched alcohols and mixtures thereof. According to a further preferred embodiment, solvent C is selected from the group consisting of $C_3$ branched alcohols, $C_4$ straight and branched alcohols, $C_5$ straight and branched alcohols, and mixtures thereof. Most preferably, solvent C is selected from the group consisting of isopropanol, 1-butanol, 2-butanol and 1-pentanol.

According to a preferred embodiment, the solvent system of the present invention comprises 0.1-20% by volume of solvent A, 7-50% by volume of solvent B and 45-92% by volume of solvent C.

According to another preferred embodiment, the solvent system comprises 1-6% by volume of solvent A, 10-40% by volume of solvent B and 54-89% by volume of solvent C.

It can furthermore be preferred that the solvent system is devoid of solvents other than solvents A, B or C. According to this embodiment, the solution does not contain solvents apart from solvents A, B and C. However, the solvent system is allowed to contain, apart from 4'-epidaunorubicin hydrochloride, other ingredients, such as for example, salts.

According to another preferred embodiment, the solvent system consists of 4'-epidaunorubicin hydrochloride, and solvents A, B and C. In this case, no further ingredients are allowed to be present in the solvent system.

The process of the present invention is preferably performed by dissolving 4'-epidaunorubicin hydrochloride in a solvent mixture I and, subsequently, contacting the resulting solution of 4'-epidaunorubicin hydrochloride with a solvent mixture II.

Solvent mixture I is characterized in comprising solvent A and having the capability to dissolve 4'-epidaunorubicin hydrochloride. Solvent mixture I is also allowed to consist only of solvent A. In this case, however, solvent mixture II must comprise solvents B and C. Nevertheless, it is preferred that solvent mixture I comprises, in addition to solvent A, also solvent B or solvent C, or a mixture of solvents B and C. In this case, it is preferred that solvent mixture I comprises (i) solvent A, on the one hand, and (ii) solvent B or C or a mixture thereof, on the other hand, in a volume ratio between 1:2 and 4:1. Preferably, the volume ratio between (i) solvent A and (ii) solvent B, C or a mixture thereof, is between 0.75:1 and 3:1, and most preferably between 1:1 and 2:1.

Solvent mixture II comprises solvent C. Solvent system II is generally allowed to consist only of solvent C. In this case, however, solvent mixture I has to comprise solvent A and solvent B. According to a preferred embodiment, solvent mixture II comprises solvents B and C.

Solvent mixture I is able to dissolve 4'-epidaunorubicin hydrochloride. Accordingly, in a first step of the process of the present invention, 4'-epidaunorubicin hydrochloride is dissolved completely in solvent mixture I. If necessary, one can assist in dissolving 4'-epidaunorubicin hydrochloride in solvent mixture I by increasing the temperature of solvent mixture I. For example, dissolution of 4'-epidaunorubicin hydrochloride in solvent mixture I can be performed at a temperature in the range between 40-80° C., preferably between 50-70° C., and most preferably between 55 and 65° C. Preferably, heating of solvent mixture I is accompanied by stirring.

Subsequently, the solution of 4'-epidaunorubicin hydrochloride in solvent mixture I is contacted with solvent mixture II. Therefore, solvent mixture II can be added to the solution of 4'-epidaunorubicin hydrochloride in solvent mixture I. On the other hand, it is also possible to add the solution of 4'-epidaunorubicin hydrochloride in solvent mixture I to solvent mixture II. The solvent mixtures can be brought into contact by every conceivable means. For example, it is possible to drop, inject or pour the 4'-epidaunorubicin hydrochloride-containing solvent mixture I in solvent mixture II or vice versa. Preferably, the solvent mixtures are brought into contact by slowly dropping the 4'-epidaunorubicin hydrochloride-containing solvent mixture I in solvent mixture II or vice versa. Dropping can be performed, for example, for a period of 1 second to 1 hour, such as 1 minute to 40 minutes, or 5 minutes to 30 minutes.

According to a preferred embodiment, upon contact of the solution of 4'-epidaunorubicin hydrochloride in solvent mixture I with solvent mixture II, the resulting solvent system comprises 0.1-20% by volume, preferably 0.1-15% by volume, more preferably 0.1-12% by volume, and most preferably 0.1-10% by volume, of solvent A.

By reducing the concentration of solvent A by means of contact with solvent mixture II not containing solvent A, solubility of 4'-epidaunorubicin hydrochloride is reduced. When the concentration of solvent A in the solvent system decreases below 20% by volume, preferably below 15% by volume, more preferably below 12% by volume, and most preferably below 10% by volume, crystallization of 4'-epidaunorubicin hydrochloride is initiated under suitable conditions. In this context, however, it has been found that decreasing the concentration of solvent A below a certain level is not sufficient to cause crystallization. It is essential that the solvent(s) used for diluting solvent A and thus to reduce the concentration of solvent A in the solvent mixture is (are) suitable solvent(s). In particular, it has been found that contacting the solution of 4'-epidaunorubicin hydrochloride in solvent A with conventionally used antisolvents, such as ethers, ketones, esters, and nitriles causes sudden precipitation of 4'-epidaunorubicin hydrochloride. In this case, amorphous 4'-epidaunorubicin hydrochloride is precipitated, which has the drawbacks mentioned above. Therefore, it is essential that the solution of 4'-epidaunorubicin hydrochloride in solvent A be contacted with solvent C. Solvent C contains a suitable alcohol which has been found to readily interact with the polar functional groups of 4'-epidaunorubicin hydrochloride. Therefore, slow crystallization instead of sudden precipitation is caused, resulting in the production of crystalline 4'-epidaunorubicin hydrochloride.

For further optimization of this process, the concentration of 4'-epidaunorubicin hydrochloride in the solvent system is adjusted to between 7 g/l and 30 g/l, preferably between 7.5 g/l and 25 g/l, and most preferably between 8 g/l and 20 g/l.

It is furthermore preferred that the pH value of the 4'-epidaunorubicin hydrochloride-containing solvent system be in a range between pH 2-5.

Furthermore, according to another preferred embodiment, after contacting the solution of 4'-epidaunorubicin hydrochloride with solvent mixture II, the resulting mixture is cooled to a temperature in the range between 5-35° C., preferably 15-30° C., and most preferably 20-30° C.

According to another preferred embodiment, the resulting mixture is cooled to a temperature in the range between 5-35° C., preferably 15-30° C. and most preferably 20-30° C., within a period of 2-8, preferably 3-7 and more preferably 4-6 hours, starting from the time of contact of solvent mixture I with solvent mixture II.

According to another preferred embodiment, the resulting mixture is stirred at a temperature in the range between 5-35° C., preferably 15-30° C. and most preferably 20-30° C., for a period of 2-24 hours, preferably 4-20 hours, more preferably 8-16 hours, even more preferably 10-14 hours.

Crystalline 4'-epidanunorubicin hydrochloride obtained by carrying out the process of the present invention preferably has the powder X-ray diffraction pattern as defined in Table 1. The powder X-ray diffraction pattern is preferably measured using $K\alpha_1$ radiation; the STOE STADI P POWDER DIFFRACTION SYSTEM (Stoe CIE GmbH, Darmstadt, Germany) is preferably used as the measuring device.

TABLE 1

Powder X-ray diffraction pattern of 4'-epidaunorubicin hydrochloride crystals according to a preferred embodiment of the present invention.

| Diffraction Angle 2 (theta) | Relative intensity P (%) |
|---|---|
| 4.98 | 15.00-17.00 |
| 5.13 | 40.00-46.00 |
| 7.23 | 15.90-17.20 |
| 7.64 | 29.00-33.50 |
| 11.37 | 7.00-8.00 |
| 12.01 | 10.90-11.50 |
| 12.18 | 23.50-26.00 |
| 16.18 | 8.50-9.80 |
| 16.77 | 18.90-20.70 |
| 17.00 | 24.50-26.90 |
| 18.46 | 9.00-10.00 |
| 18.75 | 6.80-7.30 |
| 19.24 | 10.80-12.00 |
| 19.86 | 54.00-62.00 |
| 20.22 | 16.70-18.10 |
| 21.21 | 6.90-7.50 |
| 21.82 | 25.80-28.25 |
| 22.58 | 100 |
| 23.03 | 30.00-32.00 |
| 23.44 | 14.00-15.00 |
| 24.53 | 9.3-10.60 |
| 26.55 | 8.00-9.50 |
| 26.86 | 13.40-14.60 |
| 30.59 | 8.65-9.45 |
| 32.36 | 9.70-10.70 |
| 34.82 | 6.60-7.40 |

Crystalline 4'-epidanorubicin hydrochloride of the present invention more preferably has the powder X-ray diffraction pattern as defined in Table 2. The data of Table 2 are preferably obtained with the STOE STADI P POWDER DIFFRACTION SYSTEM (Stoe CIE GmbH, Darmstadt, Germany) using $K\alpha_1$ radiation:

TABLE 2

More preferred powder X-ray diffraction pattern of 4'-epidaunorubicin hydrochloride crystals as obtained in accordance with the present invention.

| Diffraction Angle 2 (theta) | Relative intensity P (%) |
|---|---|
| 4.98 | 15.90 |
| 5.13 | 43.50 |
| 7.23 | 16.61 |
| 7.64 | 31.66 |
| 11.37 | 7.57 |
| 12.01 | 11.23 |
| 12.18 | 24.62 |
| 16.18 | 9.17 |
| 16.77 | 19.74 |
| 17.00 | 25.61 |
| 18.46 | 9.60 |
| 18.75 | 7.08 |
| 19.24 | 11.46 |
| 19.86 | 58.23 |
| 20.22 | 17.36 |
| 21.21 | 7.21 |
| 21.82 | 26.94 |
| 22.58 | 100 |
| 23.03 | 31.12 |
| 23.44 | 14.55 |
| 24.53 | 9.94 |
| 26.55 | 8.75 |
| 26.86 | 14.19 |
| 30.59 | 9.09 |
| 32.36 | 10.30 |
| 34.82 | 7.03 |

According to an even more preferred embodiment, crystalline 4'-epidaunorubicin hydrochloride of the present invention has one, more or all of the powder X-ray diffraction values (particular range of relative intensity at a particular diffraction angle 2(theta)) outlined in Table 3 as preferably measured with the STOE STADI P POWDER DIFFRACTION SYSTEM (Stoe CIE GmbH, Darmstadt, Germany) using $K\alpha_1$ radiation:

TABLE 3

Powder X-ray diffraction pattern of 4'-epidaunorubicin hydrochloride crystals according to an even more preferred embodiment of the present invention.

| Diffraction Angle 2 (theta) | Relative intensity P (%) |
|---|---|
| 5.13 | 40.00-46.00 |
| 7.64 | 29.00-33.50 |
| 12.18 | 23.50-26.00 |
| 16.77 | 18.90-20.70 |
| 17.00 | 24.50-26.90 |
| 19.86 | 54.00-62.00 |
| 21.82 | 25.80-28.25 |
| 22.58 | 100 |
| 23.03 | 30.00-32.00 |

Crystalline 4'-epidaunorubicin hydrochloride produced according to the process described herein can have the physical parameters as shown in Table 4. These data were obtained in single X-ray analysis using an instrument of Xcalibur Oxford Diffraction and MoKa (0.7107 mm$^{-1}$) as radiation source.

TABLE 4

Data of single X-ray analysis of 4'-epidaunorubicin hydrochloride as obtained in accordance with the present invention.

| Compound | [4'-epidaunorubicin]HCl |
|---|---|
| Crystal color and habit | Red prisms |
| Crystal size (mm) | 0.2 × 0.2 × 0.1 |
| Crystal system | Monoclinic |
| Space group | P21 |
| Lattice constant a (Å) | 16.5070 (11) |
| Lattice constant b (Å) | 5.4290 (4) |
| Lattice constant c (Å) | 16.9178 (9) |
| Lattice angle α (°) | 90 |
| Lattice angle β (°) | 93.164 (5) |
| Lattice angle γ (°) | 90 |
| Volume V (Å$^3$) | 1513.80 (17) |
| Density $\rho_{calc}$ (g × cm$^{-3}$) | 1.336 |
| Θ range (°) | 2.41-29.05 |

The process of the present invention allows for the production of crystalline 4'-epidaunorubicin hydrochloride having high purity, improved solubility in methanol and high thermal stability. In a single X-Ray analysis, the crystalline 4'-epidaunorubicin hydrochloride produced according to the process of the present invention preferably has monoclinic crystal structure. In the monoclinic system, the crystal is described by vectors of unequal length, as in the orthorhombic system. They form a rectangular prism with a parallelogram at its base. Hence, two pairs of vectors are perpendicular, while the third pair makes an angle other than 90°.

Therefore, the present invention provides crystalline 4'-epidaunorubicin hydrochloride which preferably has a monoclinic phase content of at least 10%. According to further preferred embodiments, the monoclinic phase content of the crystalline 4'-epidaunorubicin hydrochloride is at least 20%, at least 30%, at least 40%, at least 50%, at least 60%, at least 70%, at least 80%, at least 90%, at least 95% or at least 99%. According to a particular preferred embodiment, the crystalline 4'-epidaunorubicin hydrochloride consists only of the monoclinic form. It is further preferred that the crystalline 4'-epidaunorubicin hydrochloride of the present invention does not form part of a complex with other molecules, for example DNA, RNA or proteins.

The crystalline 4'-epidaunorubicin hydrochloride of the present invention excels in purity and shows improved solubility, in particular, in methanol. Therefore, it can be beneficially used in downstream processes for the production of anthracyclines. For example, crystalline 4'-epidaunorubicin hydrochloride can be used to produce epirubicin. The process for producing epirubicin from 4'-epidaunorubicin hydrochloride as a starting material is well-known in the art. Because of its high purity and good solubility in methanol, the use of crystalline 4'-epidaunorubicin hydrochloride as a starting material for the synthesis of epirubicin is beneficial over the use of amorphous 4'-epidaunorubicin hydrochloride.

BRIEF DESCRIPTION OF THE SEVERAL VIEWS OF THE DRAWINGS

The following figures provide supplementary information on the 4'-epidaunorubicin hydrochloride as produced according to the present invention.

DETAILED DESCRIPTION OF THE INVENTION

Figure 1:
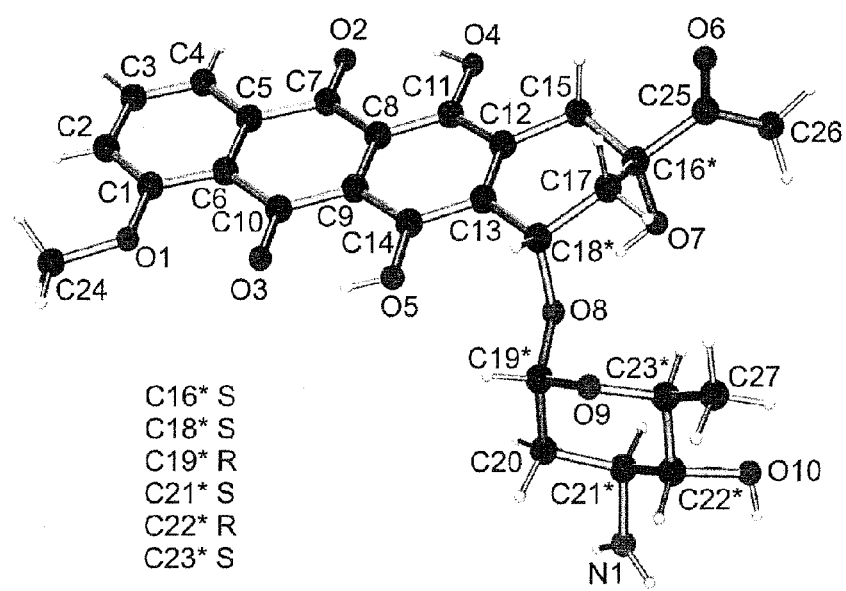
FIG. 1 is a molecular model showing the stereochemistry of 4'-epidaunorubicin hydrochloride according to single X-Ray data.
Figure 2:
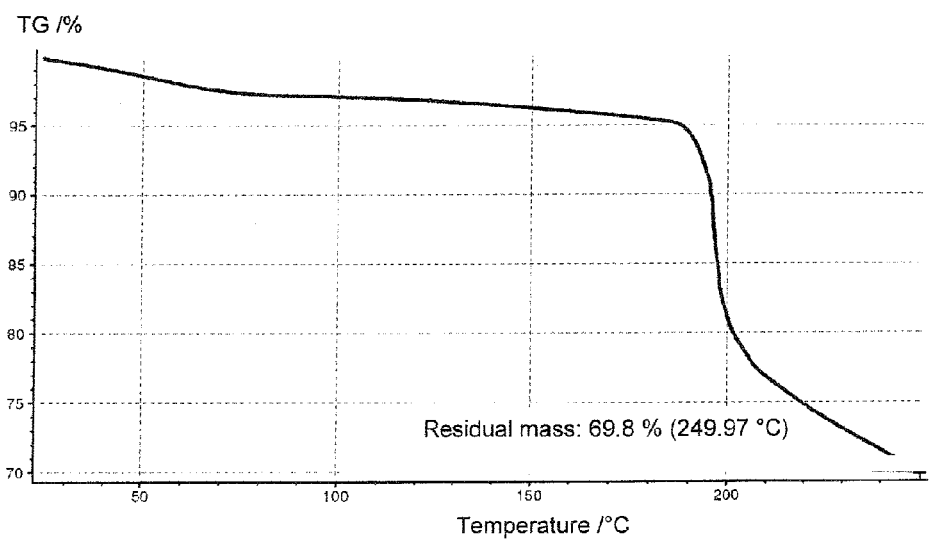
FIG. 2 is a graph showing the thermogravimetric analysis (TGA) of 4'-epidaunorubicin hydrochloride. The data were obtained using the instrument NETZSCH TG 209 (sample mass: 12.917 g, range: 24.0/10.0 (K/min)/250.0, crucible: $Al_2O_3$).

The present invention is hereinafter described by way of Examples.

Example 1

10 g 4'-epidaunorubicin hydrochloride were dissolved in a mixture of chloroform and butanol (ratio=2:1 by volume). To this mixture, 10-times the volume of a mixture of 1-propanol and 1-butanol (ratio=3:7 by volume) was added at 60° C. The end concentration of 4'-epidaunorubicin hydrochloride in the resulting solvent system was 8 g/l.

The mixture was cooled to room temperature within a period of 5 hours, and subsequently stirred for 12 hr at room temperature.

The resulting crystals were separated from the solvent mixture by means of filtration, washed with 50 ml tert-butylmethylether and dried at vacuum (<400 mbar).

The crystals were analyzed and confirmed as 4'-epidaunorubicin hydrochloride. The yield was 9.2 g, the purity was 98.2%. The product decomposed at 191° C., the mass was 528 D.

Example 2

10 g 4'-epidaunorubicin hydrochloride were dissolved in a mixture of chloroform and butanol (ratio=2:1 by volume). This mixture was slowly added to 10-times the volume of a mixture of 1-propanol and 1-butanol (ratio=3:7 by volume) at 60° C. The end concentration of 4'-epidaunorubicin hydrochloride in the resulting solvent system was 20 g/l.

The mixture was cooled to room temperature within a period of 5 hours, and subsequently stirred for 12 hr at room temperature.

The resulting crystals were separated from the solvent mixture by means of filtration, washed with 50 ml tert-butyl-methylether and dried at vacuum (<400 mbar).

The crystals were analyzed and confirmed as 4'-epidaunorubicin hydrochloride. The yield was 9.2 g, the purity was 98.2%. The product decomposed at 191° C., the mass was 528 D.

Example 3

10 g 4'-epidaunorubicin hydrochloride were dissolved in a mixture of dichloromethane and 1-propanol (ratio=1:1 by volume). To this mixture, 10-times the volume of a mixture of 1-propanol and isopropanol (ratio=2.5:8 by volume) was slowly added at 60° C. The end concentration of 4'-epidaunorubicin hydrochloride in the resulting solvent system was 8 g.

The mixture was cooled to room temperature within a period of 5 hours, and subsequently stirred for 12 hr at room temperature.

The resulting crystals were separated from the solvent mixture by means of filtration, washed with 50 ml tert-butyl-methylether and dried at vacuum (<400 mbar).

The crystals were analyzed and confirmed as 4'-epidaunorubicin hydrochloride. The yield was 9.1 g, the purity was 98.0%. The product decomposed at 190° C., the mass was 528 D.

Example 4

10 g 4'-epidaunorubicin hydrochloride were dissolved in a mixture of dichloromethane and 1-propanol (ratio=1:1 by volume). To this mixture, 10-times the volume of a mixture of 1-propanol and isopropanol (ratio=2.5:8 by volume) was slowly added at 60° C. The end concentration of 4'-epidaunorubicin hydrochloride in the resulting solvent system was 20 g.

The mixture was cooled to room temperature within a period of 5 hours, and subsequently stirred for 12 hr at room temperature.

The resulting crystals were separated from the solvent mixture by means of filtration, washed with 50 ml tert-butyl-methylether and dried at vacuum (<400 mbar).

The crystals were analyzed and confirmed as 4'-epidaunorubicin hydrochloride. The yield was 9.1 g, the purity was 98.0%. The product decomposed at 190° C., the mass was 528 D.

Comparative Example 1

4'-epidaunorubicin hydrochloride was produced and purified (by adding methanolic hydrogen chloride to a chloroform extract of 4'-epidaunorubicin hydrochloride) according to Example 2 of U.S. Pat. No. 4,345,068. As a result, 4'-epidaunorubicin hydrochloride was obtained and precipitated as an amorphous powder.

Comparative Example 2

4'-epidaunorubicin hydrochloride was produced and purified (by adding methanolic hydrogen chloride to a chloroform extract of 4'-epidaunorubicin hydrochloride) according to Example 5 of U.S. Pat. No. 4,345,068. As a result, 4'-epidaunorubicin hydrochloride was obtained and precipitated as an amorphous powder.

Comparative Example 3

4'-epidaunorubicin hydrochloride was produced and purified (by using ethanol/ether) according to Boivin et al., "Substitutions of allylic esters: preparation of 3-aminoglycals and their acid-catalyzed glycosidation. Use in the partial synthesis of glycosides of the anthracycline group," *Carbohydrate Research*, 79 (2): 193-204 (1980). As a result, 4'-epidaunorubicin hydrochloride was obtained and precipitated as an amorphous powder.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A process for producing crystalline 4'-epidaunorubicin hydrochloride comprising crystallizing 4'-epidaunorubicin hydrochloride in a solvent system including:
    a) solvent A which is selected from the group consisting of $C_1$ and $C_2$ halogenated solvents and mixtures thereof;
    b) solvent B which is selected from the group consisting of $C_1$-$C_5$ straight and branched alcohols and mixtures thereof; and
    c) solvent C which is selected from the group consisting of $C_1$-$C_5$ straight and branched alcohols and mixtures thereof, wherein solvent C is selected to provide lower solubility to 4'-epidaunorubicin hydrochloride than solvent B, wherein the process comprises steps of:
    dissolving 4'-epidaunorubicin hydrochloride in a solvent mixture I comprising (i) solvent A and (ii) solvent B or C to form a solution; and
    contacting the solution with a solvent mixture II comprising solvents B and C.

2. The process according to claim 1, wherein the solvent system comprises 0.1-20% by volume of solvent A, 7-50% by volume of solvent B and 45-92% by volume of solvent C.

3. The process according to claim 2, wherein the solvent system comprises 1-6% by volume of solvent A, 10-40% by volume of solvent B and 54-89% by volume of solvent C.

4. The process according to claim 1, wherein solvent mixture I comprises (i) solvent A and (ii) solvent B or C in a volume ratio between 1:2 and 4:1.

5. The process according to claim 1, wherein upon contacting solvent mixture I with solvent mixture II, the solvent system comprises 0.1-20% by volume of solvent A.

6. The process according to claim 1, wherein a concentration of 4'-epidaunorubicin hydrochloride in the solvent system is between 7 g/l and 30 g/l.

7. The process according to claim 1, wherein dissolution of 4'-epidaunorubicin hydrochloride in solvent mixture I is performed at a temperature in the range between 40-80° C.

8. The process according to claim 7, wherein after contacting the solution of 4'-epidaunorubicin hydrochloride with solvent mixture II the resulting mixture is cooled to a temperature in the range of 5-35° C.

9. The process according to claim 1, wherein solvent A is selected from the group consisting of chloroform and dichloromethane.

10. The process according to claim 1, wherein solvent B is selected from the group consisting of methanol, ethanol and 1-propanol.

11. The process according to claim 1, wherein solvent C is selected from the group consisting of 1-butanol, isopropanol, isobutanol, and 1-pentanol.

12. The process according to claim 1, wherein the solvent system consists of solvents A, B and C.

* * * * *